United States Patent [19]

Russell et al.

[11] 4,176,174

[45] Nov. 27, 1979

[54] VIRAL ANTIBODY DIAGNOSTIC TEST SYSTEM

[75] Inventors: Stuart M. Russell, Bromley; Leonard W. J. Bishop, Beaconsfield, both of England

[73] Assignee: Burroughs Wellcome Co., Research Triangle Park, N.C.

[21] Appl. No.: 946,439

[22] Filed: Sep. 27, 1978

Related U.S. Application Data

[63] Continuation of Ser. No. 596,989, Jul. 18, 1975, abandoned.

[30] Foreign Application Priority Data

Jul. 19, 1974 [GB] United Kingdom ............... 32050/74

[51] Int. Cl.$^2$ ..................... G01N 31/00; G01N 31/14; G01N 33/16
[52] U.S. Cl. ................................ 424/8; 23/230 B; 424/12; 424/13; 424/86; 424/89; 422/55; 422/68
[58] Field of Search .................... 424/3, 8, 12, 13, 86, 424/89; 23/230 B, 253 R

[56] References Cited

U.S. PATENT DOCUMENTS

| | | | |
|---|---|---|---|
| 3,715,427 | 2/1973 | Hirata | 424/12 |
| 3,843,777 | 10/1974 | Hainski | 424/12 |

OTHER PUBLICATIONS

Milgrom, Vox Sang., vol. 8, 1963, pp. 537–548.
Jackson, Applied Microbiol., vol. 27, 1974, pp. 896–900.
Baker, Applied Microbiol., vol. 17, 1969, pp. 422–426.
Dubois, Arch. fuer Exper. Vet. Med., vol. 24, 1970, pp. 33–59.
Kwapinski, Meth. of Immunochem. & Immunol. Res., Wiley-Intersci., N.Y. 1972, pp. 397–408, 441–464, 545–547.
Fazekas, Australian J. Exptl. Biol. Med., vol. 27, 1949, pp. 65–81.
Russell, J. Gen. Virol. vol. 27, No. 1, Apr. 1975, pp. 1–10.
Schild et al., Symp. Series Immunobiol. Standards, vol. 20, 1972, pp. 39–46.

Primary Examiner—Anna P. Fagelson
Attorney, Agent, or Firm—Donald Brown

[57] ABSTRACT

A diagnostic reagent for detecting the presence of specific microbial antibodies in body fluids which comprises a gel containing intact erythrocytes, which have appropriate microbial particles adhering directly or indirectly to the surface thereof, the gel being contained in a shallow vessel. The system may additionally include complement, or alternatively this may be added separately and after test-body fluids have been applied to the gel. Interaction of specific antibodies with the microbial particles, in the presence of complement results in the lysis of the erythrocytes thereby forming a visible positive result.

2 Claims, 1 Drawing Figure

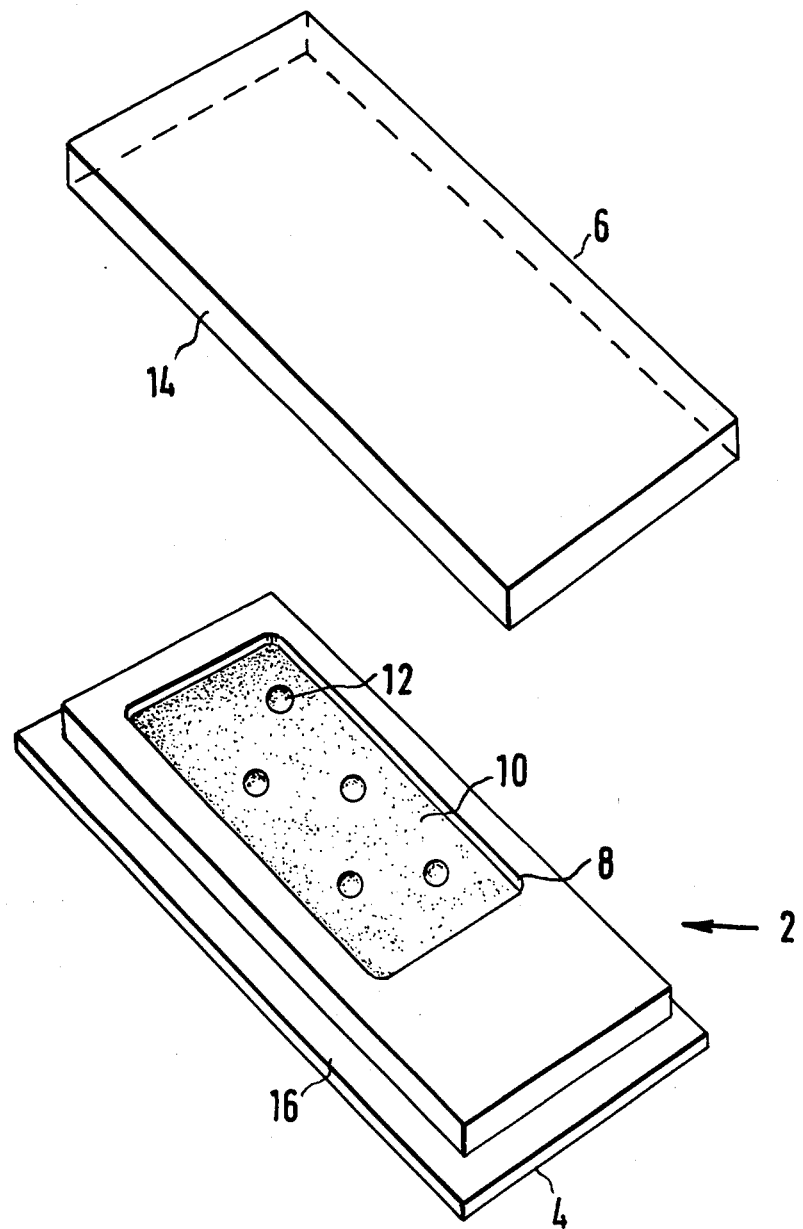

VIRAL ANTIBODY DIAGNOSTIC TEST SYSTEM

This is a continuation, of application Ser. No. 596,989 filed July 18, 1975, now abandoned.

This invention relates to a system for diagnosing microbial diseases in humans, animals and plants, and in particular for measuring the amount of antibodies produced as a result thereof.

The most common method used for the diagnosis of certain types of viral disease is the 'haemagglutinationinhibition (H.I.) test'. This test has the disadvantage that it depends on the fact that certain viruses will only agglutinate certain types of red blood cells, e.g. influenza, mumps and parainfluenza viruses agglutinate chicken, human and guinea-pig erythrocytes adenoviruses rat and monkey erythrocytes, and reoviruses and many enteroviruses only human erythrocytes. The test is performed by mixing virus with the appropriate erythrocytes in the presence of patient's serum, i.e. the fluid which is expressed when blood coagulates to form a clot. If antibodies to the virus are present in the serum, the virus will be unable to agglutinate the cells. The haemagglutination inhibition test has the further disadvantage that it is tedious and not accurate as doubling dilution series need to be used with the consequent loss of accuracy, which makes it impossible to detect small differences in antibody titre. Futhermore the sera must be pretreated to remove non-specific inhibitors that prevent the virus binding to the erythrocytes and therefore result in a false positive reading of the test.

Recently a new test for detecting influenza virus antibodies, called the 'single radial-diffusion test' has been proposed by Schild et al. (*Symp. Series Immunobiol. Standard.*, Vol. 20 1972, pp. 39–46) in which the appropriate influenza virus (67 to 100 $\mu g$ purified virus particles/ml gel) is in-corporated into agarose gel. When the gel has set circular wells are cut out and the patient's or animal's serum to be tested is introduced into the wells. The presence in the test serum of viral antibodies is detected by the appearance of zones of opalesence surrounding the wells. The opalescence is caused by the diffraction of light owing to a halo of antibody molecules surrounding each virus particle.

The single radial diffusion test has better resolution than the H.I. method and is quicker to perform. However, it does have the disadvantage that the influenza virus preparation used for the purpose has to be purified and highly concentrated in the gel, which makes the test expensive. Additionally large amounts of virus are required for the test.

It has now been found that by incorporating into a gel erythrocytes, which have microbe particles adhering to their surfaces, allowing a sample of body fluid, which may contain specific antibodies to the microbe to diffuse into the gel, introducing complement into the system, which is fixed, i.e. combines, where specific antibodies have interacted with the microbe particles, a visible circular zone of lysis will result, the size of which is dependent on the amount of antibody present. Lysis is the rupture of a erythrocytes with the resultant liberation of haemoglobin.

According to the present invention in one aspect therefore there is provided a system for detecting the presence of specific microbiol antibodies in body fluids such as blood, serum, plasma, nasal washings, cerebrospinal fluid, saliva or milk, which comprises a gel containing in-tact erythrocytes having appropriate microbe particles adhering to the surface thereof. In particular, the system as hereinbefore defined also comprises a complement.

The gel that is used is preferably made from 0.5 to 2.0% agarose but agar, gelatin or any suitable matrix which allows diffusion and does not have anti-complement activity can alternatively be used. The gel concentration should preferably be strong enough so that it is easy to handle, but not so concentrated that diffusion cannot take place.

The erythrocytes may be obtained by venipuncture of a vertebrate animal and collected in a medium that prevents clotting. Several types of erythrocytes may suitably be used for the purposes of the present invention, for instance bovine erythrocytes can be used with certain virus. Sheep erythrocytes, are however, usually used, however they have the disadvantage of having the Forssman erythrocytes antigen on their surface, and therefore the fluid to be tested may be treated prior to testing with sheep erythrocytes at 37° C. for 30 minutes in order to absorb antibodies to the Forssman antigen.

Other types may be preferred in association with particular microbes, for example when measles virus is being used Patas Monkey erythrocytes are usually very convenient and preferred although certain erythrocytes can be too fragile or larger than necessary causing less defined zones of lysis. On storage erythrocytes tend to become more fragile with age and more susceptible to spontaneous lysis, therefore in order to prolong the 'life' of the erythrocytes chemical substances may be incorporated into the gel in order to stabilize the cells. Alternatively the erythrocytes may be pretreated with a chemical substance such as gluteraldehyde, in order to stablise them.

Another method of 'prolonging the life' of the erythrocytes is to incorporate dimethylsulphoxide (DMSO) into the gel at the pouring stage and then freeze the gel in the vapour above liquid nitrogen. By incorporating about 10% DMSO the integrity of the gel is maintained.

If the microbe particles to be used in the system are viruses then these may be prepared by conventional techniques from animals, egg or tissue culture, see for example 'Textbook of Virology' by A. J. Rhodes and C. E. Van Rooyan, 5th Edition published by Williams and Wilkins, Baltmore, U.S.A. 1968.

With certain types of viruses the erythrocytes require pretreatment with a chemical substance that promotes the binding of the virus particles to the erythrocytes surface, for example, influenza virus will aggutinate erythrocytes but this is followed by elution at 37° C., i.e. the virus particles will soon detach themselves from the erythrocytes spontaneously, owing to the action of the viral enzyme neuraminidase on the erythrocytes receptors. In order to ensure that the influenza virus remains permanently attached to the erythrocytes, they may be pretreated with potassium periodate solution, the concentration of which will be dependent on the species of erythrocytes used and will vary from 1.25 to $5.5 \times 10^{-4}$ M. This results in the formation of aldehyde or similarly modified groups on the erythrocytes surface and prevents the action of neuriminidase. With other types of virus, e.g. rubella, pre-treatment of the erythrocytes with periodate, or any other chemical agent such as chromic chloride or carbodiimide may not be required.

Certain micro-organisms will not adhere directly to the erythrocytes and in such cases it may be possible to couple the organisms to the erythrocytes indirectly, using compounds having an affinity of erythrocytes, such as lectins or lipo-polysaccharides.

Complement, which in one particular type of the system is already incorporated into the gel, comprises a complex group of serum proteins, most of which have the characteristic of interacting with antibody molecules once these have combined with an antigen, the effect of such combination being to bring about lysis where the antigen concerned is a cell such as erythrocytes. The complement required for the purpose of the present invention is conveniently vertebrate complement, which may preferably be obtained commercially from Wellcome Reagents Ltd. or prepared by allowing blood to clot, removing the serum and storing it at 4° C. or below, preferably at −20° C. It is incorporated into the system in an amount sufficient to ensure lysis.

The complement may also be provided for incorporation in the system, for instance in a sealed glass or plastic vial, together with appropriate instructions for use with the gel. In addition it is convenient to provide two further sealed and sterilized vials containing reference sera, one of which contains antibodies to the microbe which has been incorporated into the system, and the other being free from such antibodies. All these essential and optional components of the system for testing body fluids for specific microbial antibodies may be presented and packaged in a box or container, together with instructions for use. It can therefore be emphasised that such a presentation of the system, comprising the gel composition, the complement and instructions as well as other optional components and aids, is considered to fall within the scope of the present invention and accordingly provide a testing kit.

The system can be adapted to distinguish between a primary challenge and a secondary challenge of a particular disease. On first infection the immune system of an individual will start to function by producing a class of immunoglobulin antibodies called IgM, which have a molecular weight of $9 \times 10^5$, approximately. As the infection progresses the immune system switches to the production of a different class of immunoglobulin antibodies called IgG, which have a smaller molecular weight of about $1.5 \times 10^5$. When the individual is challenged a second time by the same microbe the immune system will produce predominantly IgG antibodies. It has been found that a distinction between a primary challenge and a scondary challenge can be made by using in addition to the gel incorporating the specific microbe a gel, which also incorporates anti IgM serum. Such serum contains antibodies against IgM and will combine with and inactivate any IgM immunoglobulins present in the test sample of body fluid, leaving any specific IgG immunoglobulins to combine with the microbe coated erythrocytes to provide the test reaction indicating the probability of a secondary infection. Alternatively a gel which also incorporates anti IgG serum can be used to indicate that an infection is probably not a secondary challenge. Antibodies against IgG, which combine with and inactivate any undesirable IgG immunoglobulins, leaving the specific IgM immunoglobulins to combine with the microbe coated erythrocytes, may therefore be obtained and isolated and incorporated into a gel and therefore provide the test reaction indicating a primary challenge.

In a further particular aspect therefore the system may comprise a composition as hereinbefore defined, and also an effective amount of an anti-immunoglobulin serum.

Such anti-immunoglobulin sera, particularly anti IgM rich fractions or preparations, may be obtained, commercially from Wellcome Reagents Ltd, or by purifying sera from myeloma patients, for instance on DEAE cellulose in order to remove unwanted immunoglobulins, adding adjuvant and injecting into animals. The animals are later bled and the sera are removed and can be used for incorporation into the gel.

The system may also be adapted to detect particular haemagglutinin and neuramiidase antigens on influenza virus particles, by using various recombinant strains of influenza virus.

The vessel into which the gel is poured conveniently comprises a plastic or glass plate which has a plain rectangular recess suitable for containing the gel layer, and a flat, transparent rectangular glass or plastic plate which can be placed over the plate with the recess, in order to keep the gel moist, sterile and prevent evaporation. Alternatively a Petri dish or any suitable container can be used as long as the thickness of the system is not less than about 0.1 mm and not greater than 5 mm. In addition the gel must have an even thickness.

The vessels used are normally packed under sterile conditions and therefore require no further sterilizing treatment. In order to prevent the unwanted growth of bacteria or fungi on the finished gel a bacteriocidal and fungicidal agent such as sodium azide or Methiolate is incorporated into the gel. Therefore the sodium azide has the property of prolonging the storage life of the complement if it is incorporated into the gel.

The sample of body fluid for testing with the system as hereinbefore defined, may be obtained from the patient or animal by several different methods depending on the particular fluid being tested. For instance blood can be obtained by venopuncture. If serum is to be used for the test, it is preferably heated to 56° C. and held at that temperature for 30 minutes in order to remove any complement present. The samples can be applied to the gel either by deposition in a well cut out of the gel, or adsorption onto a circle of filter paper having a diameter of 4–5 mm, which in turn is placed on the surface of the gel.

Where specific microbial antibodies are present in the sample of fluid, a circular and visible zone of lysis is produced, whenever the complement is already present in the gel or introduced subsequent to the fluid, the size of which is positively related to the logarithm of the antibody titre.

In yet a further method of distinguishing between a primary and secondary challenge of a disease a well is cut of the centre of a gel, into which the test fluid is placed. At equal distances from the central well at least two other wells are cut out, into one of which is placed anti IgM serum and into a second is deposited anti IgG serum. The gel is incubated to allow zones of lysis to develop and where a half moon portion of no haemolysis occurs at the edge of the haemolysis zone, near one of the surrounding wells, this shows that a paticular class of immunoglobulins e.g. IgM, were present in the test fluid, and have therefore been neutralized. Presence of IgM immunoglobulins in the test fluid indicate a primary challenge of the disease.

In a second aspect of the invention there is provided a method of detecting the presence of microbial antibodies in body fluids which comprises applying a sample of body fluid, such as blood, serum, plasma, nasal washings, cerebrospinal fluid, saliva or milk from a patient or animal, to a diagnostic system, as hereinbefore defined, allowing the fluid to diffuse into the gel and interact with the components of the system also including a complement or introducing complement into the gel, to provide a visible zone of erythrocytes lysis corresponding to the amount of microbial antibody in the body fluid.

The method of detecting microbial antibodies describes may be used for diagnosing many diseases, for example viral diseases such as influenza, both A & B, rubella, measles, parainfluenza, cytomegalovirus and louping ill. The test is especially useful for detecting those people or animals who have no immunity or low levels of immunity to a particular disease and therefore are at risk and require vaccination. The test can also be used for diagnosing virus diseases in plants. A preparation of diseased plant tissue is injected into an animal and after a period of time serum, which contains antibodies to the plant virus, is removed from the animal and used in the test. The test can also be used for detecting antibodies to psittacosis, Mycoplasma as well as bacteria.

The advantages of this method in the viral field over previously used methods are that it is quick, simple and easy to carry out, and it is very specific since it can distinguish between antisera to closely related strains of a virus, particularly strains of influenza virus, and may even differentiate between primary and secondary infection. The advantage of the system provided by the invention is that, compared with the Schild technique, no purification or concentration of the virus may be needed, indeed with influenza virus crude allantoic fluid may be used. In addition the visible area of the lysis provides antibody levels within an accuracy of 5 to 20%.

A Hyland plate suitable for containing the gel according to the invention will now be described with reference to the accompanying drawing. The Hyland plate 2 comprises a plain rectangular base 4 and a lid 6, both made from a transparent plastic material. The base 4 has a rectangular recess 8 into which a gel 10 is poured. Wells 12 are cut out of the gel 10 in order to receive body fluid samples. The lid 6 fits tightly over the base 4 in order to protect the gel from drying and physical damage. The lid 6 is surrounded by a rim 14 which engages a lip which surrounds the base 4.

The invention will now be described with reference to the following Examples but is in no way to be considered limited by the same.

EXAMPLE 1

Equal volumes of washed packed sheep erythrocytes and a $5.5 \times 10^{-4}$ M solution of potassium periodate in saline were mixed and allowed to stand at room temperature for 10 minutes. Allantoic fluid, from chicken eggs, containing influenza virus strain A2 (haemagglutination titre approximately $4 \times 10^3$/ml) was added, the volume of the fluid being ten times that of the packed erythrocytes. The mixture was left at room temperature for 10 minutes, the coated erythrocytes were then washed three times in Barbitone buffered saline i.e. saline containing barbitone and buffered at pH 7.2, to remove free virus not attached to the erythrocytes, and finally made up to a 50% v/v suspension in buffered saline.

1% Agarose was made up in Barbitone buffered saline, and an aliquot (1.5 ml) of this was poured into a Hyland plate to form a base layer (1 mm thick). A sample (100 μl) of the 50% erythrocytes suspension was mixed with agarose (1.5 ml) at 45° C. and the resultant suspension was poured on top of the base layer and allowed to solidify to form a test system having a even thickness (2 mm).

EXAMPLE 2

The 50% v/v virus coated erythrocyte suspension was prepared as in Example 1. A portion (100 μl) of this was added to agarose (3 ml) and to this was added guinea pig complement solution (100 μl of 1:160 haemolytic titre) obtainable from Wellcome Reagents Ltd. The resultant suspension was poured into a Hyland plate and allowed to solidy to give an even layer (2 mm thick).

EXAMPLE 3

A 1% solution of Agarose was made up in Barbitone buffered soline and to this was added sufficient sodium azide to give a 0.1% solution. A suspension containing virus coated erythrocytes and guinea pig complement was then prepared as in Example 2, using the agarose solution and an aliquot (3 ml) was then poured into a Hyland plate.

EXAMPLE 4

A virus coated erythrocytes suspension was prepared as in Example 1. After leaving at room temperature for 10 minutes the cells were washed once, then 1 ml of the packed cells were treated with 0.5 ml of 1% gluteraldehyde solution for $7\frac{1}{2}$ minutes. The cells were then washed four times to remove excess gluteraldehyde and a gel plate was then prepared as described in Example 1.

EXAMPLE 5

A gel was prepared as in Example 1, except that the virus used was rubella, BHK grown Thomas strain (haemagglutination titre approximately 1024/ml). The erythrocytes and rubella virus were allowed to stand for 1 hour at 4° C. to allow for adsorption. In addition 0.1% sodium azide was incorporated into the agarose gel.

A sample of patients blood was placed on an area of filter paper (whatman) in an amount sufficient that discs (4 mm diameter) cut out of it each contained $2.3 \times 10^{-2}$ ml of blood adsorbed thereon. The blood soaked discs were then placed on top of the gel left at 4° C. overnight and the incubated at 37° C. for 3 hours, at the end of which time any zone of lysis under each filter paper disc indicated that the patient had antibodies in their blood to rubella.

EXAMPLE 6

A gel was prepared as in Example 1 except that the virus used was louping ill (haemagglutination titre 1:256). The erythrocytes were treated with an equal volume of $10^{-3}$ M potassium periodate before being left to stand with the virus for 45 minutes at 4° C. to allow for adsorption. The standard procedure for preparation of the plate, as described in example 1, was then carried out.

EXAMPLE 7

A gel was prepared as in Example 1 except that the erythrocytes used were Patas Monkey cells and the virus used was measles virus (haemagglutination titre 1:1024). The Patas Monkey erythrocytes are treated with an equal volume of $10^{-3}$ M potassium periodate before being left to stand with the virus for 15 minutes at 37° C. The standard procedure for preparation of the plate, as described in example 1, was then carried out.

EXAMPLE 8

A gel was prepared as in example 1 except that the microorganism used was Psittacosis (complement fixation titre 1:64). Erythrocytes and Psittacosis organisms were allowed to stand for 1 hour to allow for adsorption. The standard procedure for preparation of the plate, as described in example 1, was then carried out.

EXAMPLE 9

A gel was prepared as in Example 1 except that the microorganism used was *Mycoplasma gallisepticum* (haemagglutination titre 1:64). The periodate treated erythrocytes were mixed with 2.0 ml of a sonicated 1 in 5 dilution of the Mycoplasma preparation and left to stand for 20 minutes. The standard procedure for preparation of the plate, as described in example 1, was then carried out.

EXAMPLE 10

A gel was prepared as in Example 1 except that the micro-organism used was *Bordetella pertussis*. The erythrocytes and Bordetella organisms were allowed to stand for an hour at 4° C., with intermittent shaking, to allow for adsorption. In addition 0.1% sodium azide was incorporated into the agarose gel. The standard procedure for preparation of the plate, as described in Example 1, was then carried out.

EXAMPLE 11

A gel was prepared as in Example 10 except that the micro-organism used was *Vibrio cholerae Inaba*.

EXAMPLE 12

A suspension was prepared as in Examples 1,2,3,5,6,7,8,9 or Example 10, which in addition included anti IgM immunoglobulin serum obtained from Wellcome Reagents Ltd. The resultant suspension was then poured into a Hyland plate.

EXAMPLE 13

A patient suspected of suffering from influenza strain A2 provided samples of blood.

A test system was prepared as in Examples 1.2 and 3 and wells (3 mm diameter) were punched out. To each well was added an aliquot (10 µl) of the test body fluid e.g. serum, which had previously been heated to 56° C. and held at that temperature for 30 minutes in order to inactivate it. The system was kept overnight in a moist box at a reduced temperature (4° C.) in order to allow the completion of diffusion. After diffusion the system was covered with a solution of guinea pig complement (1 ml of a freeze dried preparation obtainable from Wellcome Reagents Ltd., and reconstituted with distilled water according to the instructions on the container) and then incubated (37° C.) until zones of lysis developed (2-3 hours) which indicated that the patient has at some time suffered from type $A^2$ influenza. The system was then washed to remove complement and released haemoglobin and it was finally fixed in Formal Saline (10%) for storage and reference purposes. The diameter of the zones of lysis produced were then measured, and compared with calibrated reference zones.

EXAMPLE 14

A gel was prepared as in Example 2, except that the virus used was Rubella, and a well (3 mm diameter) was cut out of the centre. Two further wells were cut out at equal distances from the central well. Into the centre well an aliquot (10 µl) of the test fluid was put, and into the other wells a volume (10 µl) of IgG serum was deposited.

The gel was incubated until zones of lysis developed.

The zones of lysis were examined and in the part of the zone nearest the IgG well and half moon portion pointing towards the test fluid well, of no haemolysis was visible, which showed that IgG immunoglobulin molecules were present in the test fluid and had been neutralized.

EXAMPLE 15

A kit for use in diagnosing influenza A2 or for detecting the presence of influenza A2 antibodies is composed of a vial containing a freeze dried preparation of reference serum, one serum containing specific influenza A2 antibodies and the other not. Also contained in the kit are Hyland plates containing the system as prepared in either Example 1 or 4 together with instructions for use as set out in Example 5.

EXAMPLE 16

A kit for use in diagnosing influenza A2 strain or for detecting the presence of influenza A2 antibodies is composed of two vials each containing a freeze preparation of reference serum, one containing specific influenza A2 antibodies and the other not, together with Hyland plates containing the system as prepared in any of Example 2,3 or 4, together with instructions for use.

We claim:

1. A specific viral antibody detecting diagnostic system suitable for measuring the amount of antibodies in a test fluid comprising a layer of gel from 0.1 to 5 mm thick, which contains:
    (a) intact erythrocytes having appropriate viruses adhering to the surface thereof;
    (b) an erythrocyte preservative;
    (c) a bacteriocidal/fungicidal agent; and wherein one or more wells are cut in the gel for receiving test fluid.

2. A specific rubella antibody detecting diagnostic system suitable for measuring the amount of antibodies in a test fluid comprising a layer of gel from 0.1 to 5 mm thick, which contains:
    (a) intact erythrocytes having rubella virus adhering to the surface thereof;
    (b) an erythrocyte preservative;
    (c) a bacteriocidal/fungicidal agent; and wherein one or more wells are cut into the gel for receiving test fluid.

* * * * *